(12) United States Patent
Barthel et al.

(10) Patent No.: US 11,547,721 B2
(45) Date of Patent: Jan. 10, 2023

(54) MAGNETIC NANOPARTICLES FOR USE IN THE TREATMENT OF TUMORS

(71) Applicants: CONSIGLIO NAZIONALE DELLE RICERCHE, Rome (IT); FONDAZIONE IRCCS ISTITUTO NAZIONALE DEI TUMORI, Milan (IT); FONDAZIONE ISTITUTO ITALIANO DI TECNOLOGIA, Genoa (IT); UNIVERSIDADE DE SANTIAGO DE COMPOSTELA, Santiago de Compostela (ES); UNIVERSITA DEGLI STUDI DI GENOVA, Genoa (IT)

(72) Inventors: Markus Barthel, Genoa (IT); Marco Cassani, Sedriano (IT); Mariangela Figini, Milan (IT); Juan Granja, Santiago de Compostela (ES); Teresa Pellegrino, Genoa (IT); Alessandra Quarta, Novoli (IT)

(73) Assignees: UNIVERSIDADE DE SANTIAGO DE COMPOSTELA, Santiago de Compostela (ES); FONDAZIONE IRCCS ISTITUTO NAZIONALE DEI TUMORI, Milan (IT); FONDAZIONE ISTITUTO ITALIANO DI TECNOLOGIA, Genoa (IT); UNIVERSITA DEGLI STUDI DI GENOVA, Genoa (IT); CONSIGLIO NAZIONALE DELLE RICERCHE, Rome (IT)

(*) Notice: Subject to any disclaimer, the term of this patent is extended or adjusted under 35 U.S.C. 154(b) by 282 days.

(21) Appl. No.: 17/051,329

(22) PCT Filed: May 3, 2019

(86) PCT No.: PCT/IB2019/053636
§ 371 (c)(1),
(2) Date: Oct. 28, 2020

(87) PCT Pub. No.: WO2019/215560
PCT Pub. Date: Nov. 14, 2019

(65) Prior Publication Data
US 2021/0052637 A1 Feb. 25, 2021

(30) Foreign Application Priority Data
May 7, 2018 (IT) .................. 102018000005104

(51) Int. Cl.
| A61K 33/243 | (2019.01) |
| A61K 47/60 | (2017.01) |
| A61K 47/68 | (2017.01) |
| A61K 47/52 | (2017.01) |
| A61K 9/16 | (2006.01) |
| A61P 35/00 | (2006.01) |

(52) U.S. Cl.
CPC ............ *A61K 33/243* (2019.01); *A61K 9/167* (2013.01); *A61K 47/52* (2017.08); *A61K 47/60* (2017.08); *A61K 47/6803* (2017.08); *A61P 35/00* (2018.01)

(58) Field of Classification Search
CPC .. A61K 33/243; A61K 47/60; A61K 47/6803; A61K 47/52; A61K 9/167; A61P 35/00
See application file for complete search history.

(56) References Cited

U.S. PATENT DOCUMENTS

| 2011/0044911 A1* | 2/2011 | Akhtari | ............. A61K 41/0052 424/9.4 |
| 2011/0060036 A1* | 3/2011 | Nie | ........................ A61K 47/56 977/773 |

OTHER PUBLICATIONS

Babincova et al., "Radiation enhanced efficiency of combined electromagnetic hyperthermia and chemotherapy of lung carcinoma using cisplatin functionalized magnetic nanoparticles", Pharmazie, 2014, vol. 69, No. 2, pp. 128-131.
Gogineni et al., "Abstract 4105: Localized and triggered release of oxaliplatin for the treatment of colorectal liver metastasis", Cancer Research, 2018, vol. 78, No. 13, pp. 1-4.
Gomez Blanco et al., "Iron oxide nanocubes with high r2 relaxivity decorated with pt(IV) prodrug for multimodal imaging and cancer therapy", 2nd Early Career Researchers' Meeting for the British Society for Nanomedicine, 2016, vol. 1, Issue 2, p. 54.
Kolosnjaj-Tabi et al., "Heat-Generating Iron Oxide Nanocubes: Subtle "Destructurators" of the Tumoral Microenvironment", ACS Nano, 2014, vol. 8, No. 5, pp. 4268-4283.
Gao et al.,"Tumor Penetrating Theranostic Nanoparticles for Enhancement of Targeted and Image-guided Drug Delivery into Peritoneal Tumors following Intraperitoneal Delivery", Theranostics, 2017, vol. 7, Issue 6, pp. 1689-1704.
Kakwere et al., "Functionalization of Strongly Interacting Magnetic Nanocubes with (Thermo)Responsive Coating and Their Application in Hyperthermia and Heat-Triggered Drug Delivery", ACS Applied Materials & Interfaces, 2015, vol. 7, No. 19, pp. 10132-10145.
International Search Report and Written Opinion for Corresponding International Application No. PCT/IB2019/053636 (13 Pages) (dated Aug. 7, 2019).

* cited by examiner

*Primary Examiner* — Michael P Cohen
(74) *Attorney, Agent, or Firm* — Lucas & Mercanti, LLP

(57) ABSTRACT

The present invention relates to magnetic nanoparticles based on iron oxide having cubic shape, suitably functionalized for the release of targeting chemotherapeutic agents, i.e. selectively in the tumors being treated The invention also relates to the pharmaceutical compositions having such nanoparticles and to their use in combined oncological therapies of hyperthermia and chemotherapy, useful in particular in the treatment of ovarian tumors.

10 Claims, 7 Drawing Sheets
Specification includes a Sequence Listing.

SEQUENCE LISTING

```
<160> NUMBER OF SEQ ID NOS: 2

<210> SEQ ID NO 1
<211> LENGTH: 281
<212> TYPE: PRT
<213> ORGANISM: Artificial Sequence
<220> FEATURE:
<223> OTHER INFORMATION: scFv antibody fragment

<400> SEQUENCE: 1

Met Lys Tyr Leu Leu Pro Thr Ala Ala Ala Gly Leu Leu Leu Leu Ala
1               5                   10                  15

Ala Gln Pro Ala Met Ala Asn Val Gln Leu Val Glu Ser Gly Gly Gly
            20                  25                  30

Leu Val Gln Pro Gly Arg Ser Leu Arg Leu Ser Cys Thr Thr Ser Gly
        35                  40                  45
```

Phe Thr Phe Gly Asp Tyr Ala Met Ile Trp Ala Arg Gln Ala Pro Gly
    50                  55                  60

Lys Gly Leu Glu Trp Val Ser Ser Ile Ser Ser Ser Ser Tyr Ile
65              70                  75                  80

Tyr Tyr Ala Asp Ser Val Lys Gly Arg Phe Thr Ile Ser Arg Asp Asn
            85                  90                  95

Ala Lys Asn Ser Leu Tyr Leu Gln Met Asn Ser Leu Arg Ala Glu Asp
        100                 105                 110

Thr Ala Val Tyr Tyr Cys Ala Arg Glu Arg Tyr Asp Phe Trp Ser Gly
        115                 120                 125

Met Asp Val Trp Gly Lys Gly Thr Thr Val Thr Val Ser Ser Gly Gly
    130                 135                 140

Gly Gly Ser Gly Gly Gly Ser Gly Gly Ser Ala Gln Ser Ala Leu
145                 150                 155                 160

Thr Gln Pro Ala Ser Val Ser Gly Ser Pro Gly Gln Ser Ile Thr Ile
            165                 170                 175

Ser Cys Thr Gly Thr Ser Ser Asp Val Gly Ser Tyr Asn Leu Val Ser
        180                 185                 190

Trp Tyr Gln Gln His Pro Gly Lys Ala Pro Lys Leu Met Ile Tyr Glu
        195                 200                 205

Gly Ser Lys Arg Pro Ser Gly Val Ser Asn Arg Phe Ser Gly Ser Lys
    210                 215                 220

Ser Gly Asn Ala Ala Ser Leu Thr Ile Ser Gly Leu Gln Ala Glu Asp
225                 230                 235                 240

Glu Ala Asp Tyr Tyr Cys Gln Ser Tyr Asp Ser Ser Leu Ser Val Val
            245                 250                 255

Phe Gly Gly Gly Thr Lys Leu Thr Val Leu Gly Ala Ala Ala His His
            260                 265                 270

His His His His Gly Ala Ala Glu Gln
        275                 280

<210> SEQ ID NO 2
<211> LENGTH: 843
<212> TYPE: DNA
<213> ORGANISM: Artificial Sequence
<220> FEATURE:
<223> OTHER INFORMATION: DNA coding for scFv C4 fragment

<400> SEQUENCE: 2
atgaaatacc tattgcctac ggcagccgct ggattgttat tactcgcggc ccagccggcc      60
atggccaacg tgcagctggt ggagtctggg ggaggcttgg tacagccagg gcggtccctg     120
agactctcct gcacaacttc tggattcact tttggtgatt atgctatgat ctgggcccgc     180
caggctccag gaagggggct ggagtgggtc tcatccatta gtagtagtag tagttacata     240
tactacgcag actcagtgaa gggccgattc accatctcca gagacaacgc caagaactca     300
ctgtatctgc aaatgaacag cctgagagcc gaggacacgg ctgtgtatta ctgtgcgaga     360
gaacgatacg attttggag tggaatggac gtctggggca aagggaccac ggtcaccgtc     420
tcgagtggtg gaggcggttc aggcggaggt ggctctggcg gtagtgcaca gtctgccctg     480
actcagcctg cctccgtgtc tgggtctcct ggacagtcga tcaccatctc ctgcactgga     540
accagcagtg atgttggag ttataacctt gtcctggt accaacagca cccaggcaaa     600
gcccccaaac tcatgattta tgagggcagt aagcggccct caggggtttc taatcgcttc     660
tctggctcca agtctggcaa cgcggcctcc ctgacaatct ctgggctcca ggctgaggac     720

```
gaggctgatt attactgcca gtcctatgac agcagcctga gtgtggtatt cggcggaggg    780
accaagctga ccgtcctagg tgcggccgca catcatcatc accatcacgg ggccgcagaa    840
caa                                                                  843
```

MAGNETIC NANOPARTICLES FOR USE IN THE TREATMENT OF TUMORS

CROSS-REFERENCE TO RELATED APPLICATIONS

This application is a 371 of PCT/IB2019/053636, filed May 3, 2019, which claims the benefit of Italian Patent Application No. 102018000005104 filed May 7, 2018.

FIELD OF THE INVENTION

The present invention relates in general to the pharmaceutical field, and more precisely it refers to magnetic nanoparticles based on cubic iron oxide, suitably functionalized for the targeted release of chemotherapeutic drugs, for use in combined oncological therapies of hyperthermia and chemotherapy.

STATE OF THE ART

Oncological hyperthermia is a type of therapy used in the treatment of tumors, which consists in the selective administration of heat to a tumor tissue so as to locally increase the temperature above 42° C. Most of the tumor cells are not irrorated by a regular vascular system, and are unable to dissipate the excess of heat received, so that they are strongly damaged, if not destroyed, by hyperthermal treatment. On the contrary healthy cells, well irrorated, dissipate more easily the excess of heat and suffer minor damages as a result of such treatments. Therefore, healthy tissues adjacent to the tumor do not suffer significant damages and, more generally, hyperthermia has not shown relevant side toxic effects.

There are different types of hyperthermia treatments depending on how the tumor tissue is warmed up. One of the most selective methods for targeted hyperthermia is the use of magnetic nanoparticles capable of localizing in tumors: these are particles that generate heat on-site if activated by the application of alternating magnetic fields—applied externally to the body of the patient—thus causing the desired heating of the tissue; this type of hyperthermia is known as magnetic hyperthermia. Among the most studied magnetic materials proposed for these therapies, also given their availability and biocompatibility, there are iron oxide nanocrystals such as magnetite or maghemite.

Several methods are known for the synthesis of these materials, which have become increasingly refined in recent years in order to have nanomaterials not only having magnetic properties suitable for application in hyperthermia, but having a high regularity of shape and size and therefore capable of high performance. In the literature, for example, nanosystems based on spherical $Fe_2O_3$ iron oxide nanoparticles have been described for use in oncological hyperthermia, in particular capable of localization in ovarian tumor cells (see Quarta, A. et al. Nanoscale, 2015 7(6): p. 2336-51). In addition to these spherical nanoparticles, systems based on cubic nanoparticles are also known, which have proved to be even more efficient than spherical particles as mediators of heating in hyperthermia treatments, (see for example Kolosnjaj-Tabi, J. et al. Acs Nano, 2014 8 (5): p. 4268-4283).

Oncological hyperthermia has been particularly useful in the so-called combined therapies, in which this type of treatment is in fact combined with other oncological therapies such as radiotherapy and chemotherapy. Clinical studies have indeed shown that combining a hyperthermia treatment of tumors with one or both of these classic cancer therapies increases their effectiveness, without increasing the overall toxicity of the treatments and therefore without increasing damages to healthy organs, improving patient tolerance to treatments and often prolonging their survival. The medical indications for hyperthermia in these combined therapies also concern various types of tumors, for which such therapies have proved particularly effective.

It is therefore evident from what has been explained above how the need to have magnetic nanoparticle systems that are efficient heat mediators for heating the tumor in hyperthermia treatments and at the same time facilitate at the same time is strongly felt in the field of oncological medical treatments. the administration of a chemotherapeutic agent, and can therefore be used in combination therapies of hyperthermia and chemotherapy to obtain even better therapeutic results and at the same time limited side effects.

SUMMARY OF THE INVENTION

Applicants have now developed magnetic nanoparticles that have proven to be efficient heat mediators in heating tumor cells in magnetic hyperthermia treatments and at the same time are capable of going to localize themselves selectively in these cells, also carrying a chemotherapeutic agent, so as to realize an effective system of combined oncological therapy.

Subject of the invention is therefore a magnetic nanoparticle based on iron oxide in the form of a nanocube, having a polymeric coating with hydrophilic groups on the surface, functionalised with a platinum-based chemotherapeutic agent and a targeting agent comprising an antibody fragment, whose essential characteristics are defined in the first of the appended claims.

A further subject of the present invention is represented by a process for preparing the nanoparticles, as defined in claim 6 herein annexed.

Still a further subject of the present invention is represented by a pharmaceutical composition comprising a plurality of the aforementioned nanoparticles, and by the nanoparticle itself or by the composition for use as a medicament, in particular in combined oncological therapies of hyperthermia and chemotherapy, as defined respectively in the claims 7, 8 and 9 annexed herein.

Further important characteristics of the nanoparticles, of the compositions and of their use according to the present invention are defined in the dependent claims annexed herein.

BRIEF DESCRIPTION OF THE FIGURES

In FIGS. 5b and 5c by "NCs_scFv" are indicated the nanocubes functionalized with the antibody fragment only, while by "NCs_Peg-Pt_scFv" are indicated the nanocubes of the invention, functionalised with the antibody fragment and also comprising the chemotherapeutic agent.

DETAILED DESCRIPTION OF THE INVENTION

The present invention provides a novel magnetic nanoparticle based on iron oxide having a cubic shape, functionalized with a platinum-based chemotherapeutic agent and with a targeting agent, comprising an antibody or a fragment thereof having a specificity against an over-expressed receptor in a given form of a tumor; this nanoparticle is useful for achieving a combined oncological therapy of hyperthermia and chemotherapy towards that tumor form.

Thanks to the functionalization of iron oxide-based magnetic nanocubes, already known for example from U.S. Pat. No. 9,376,328, the Applicants have succeeded in the objective of imparting very precise biomedical functions to nanoparticles which are inert per se, without any biological effect, although known for their efficacy in hyperthermia treatments. As illustrated in the following experimental part, the possibility of providing with the present nanoparticles a double oncology treatment on the same tissue has, not only a greater therapeutic effect than the two separate treatments but it has shown an actual synergy between hyperthermia and chemotherapy treatments.

The stable functionalization of the single nanoparticle is obtained according to the invention by first activating the surface of the nanoparticle with a polymeric coating, then attaching to this coating the bioactive molecules of interest, tumor targeting agent and chemotherapeutic agent, which allow the nanoparticle to locate in the tumor tissue and to induce therein the cells death. The covalent bond between the polymer coating and the targeting agent and between the coating and the chemotherapeutic agent is achieved thanks to the carboxy groups which the coating has on the surface of the nanoparticle and to linker derivatives of amino-poly (ethylene glycol), that are the same or different from each other.

The nanoparticles of the invention are based on the use of magnetic oxide-based nanoparticles having cubic shape. For this reason, the terms "nanoparticles" and "nanocubes" will be used indifferently in the following. The present iron oxide nanoparticles in cubic form can be prepared for example as described in U.S. Pat. No. 9,376,328; starting from minerals based on iron oxide such as magnetite, ferrite or maghemite. These nanoparticles have a characteristic cubic shape, nanometric dimensions and a monodisperse particle size distribution, showing substantially uniform size and shape.

The polymeric coating of the nanocubes is preferably obtained with an amphiphilic polymer, such as for example poly (maleic anhydride-alt-1-octadecene), having hydrophobic chains which bind to the nanoparticle and hydrophilic portions comprising carboxylic groups which remain exposed on the surface, creating a true hydrophilic coating that can be used for functionalisations and for making hydrophobic nanoparticles soluble in polar media.

Figure 1:
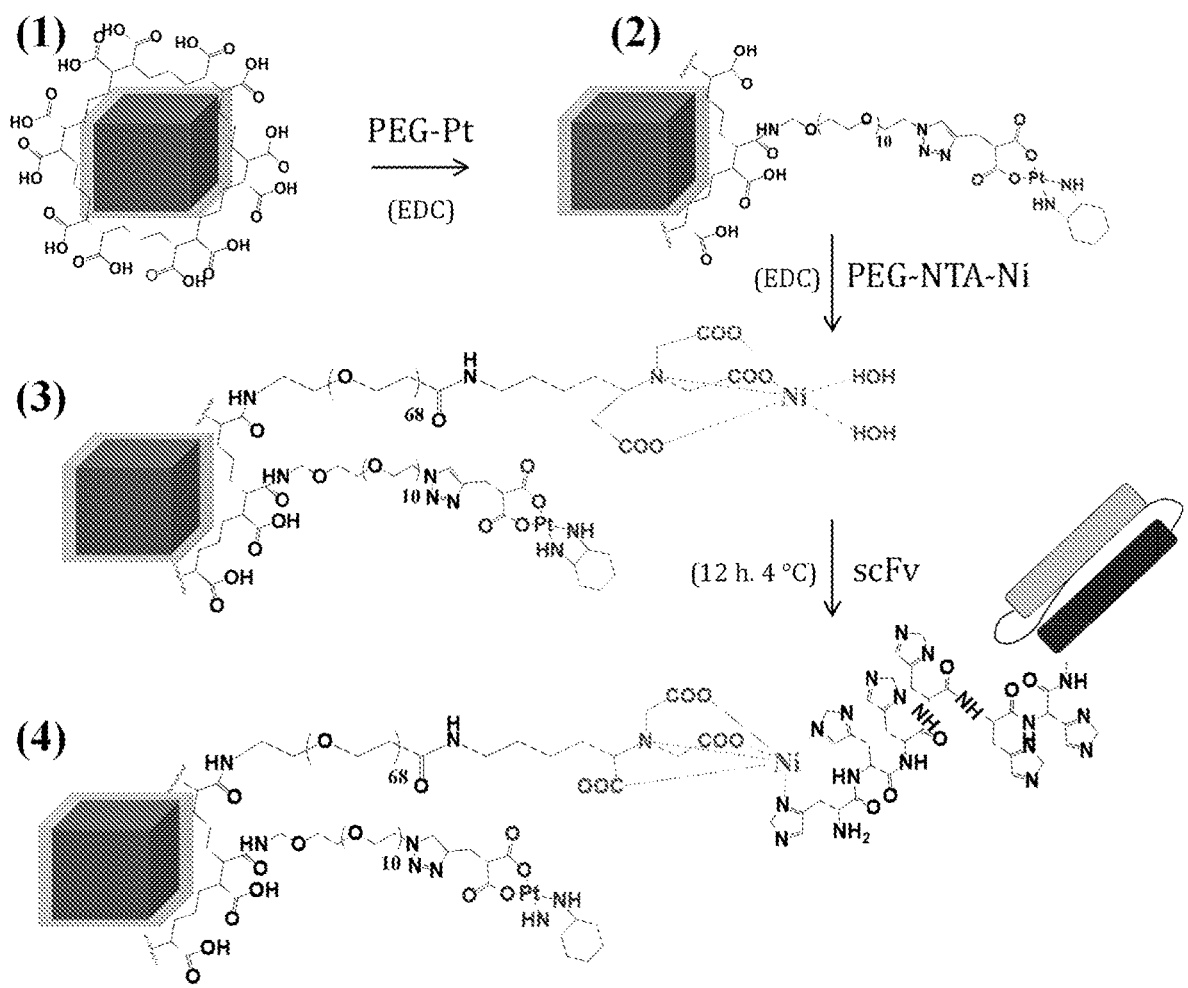
FIG. 1 schematically shows the steps for the preparation of the functionalized nanoparticle of the invention according to a preferred embodiment described in detail in the following.

The platinum-based chemotherapeutic agent is bound to a first linker comprising a poly (ethylene glycol) chain, in its turn linked to the polymer coating of the nanoparticle with covalent bonds, for example with an amide bond between the acidic groups of the maleic anhydride on the coating and amino groups as linker's terminals (see FIG. 1). The covalent bond between the chemotherapeutic agent and the linker of poly(ethylene glycol) preferably takes place via a pH-responsive group, consisting for example of a group comprising platinum-binding di-carboxylic acid functionalities in the chemotherapeutic agent, so that changes in pH, in particular lowering of the pH by acidification, can break this covalent bond and assist the release of the chemotherapeutic agent.

Chemotherapeutic agents of possible use according to this invention are in general the chemotherapeutic agents comprising platinum; preferably the chemotherapeutic agent is oxaliplatin.

The targeting agents according to the invention comprise a scFv antibody fragment (single chain variable fragment) capable of binding, directly by means of an adequate binding portion or through a suitable spacer, to a second linker comprising an amino-poly (ethylene glycol) chain, capable of binding in its turn with the carboxyl groups of the coating on the nanoparticle. By an adequate binding portion of the antibody fragment for example a histidine sequence or histidine "tag" is meant. In a particular embodiment, for example the amino-poly (ethylene glycol) linker is an amino-polyethylene glycol derivative with a complex of $Ni^{2+}$ of nitrilotriacetic acid which binds to said targeting agent by complexation of $Ni^{2+}$ with the aforementioned histidines comprised in the antibody fragment.

According to an embodiment of the present invention the scFv fragment is an antibody fragment named C4 which binds specifically to the folate receptor $Fr_\alpha$ and has the amino acid sequence SEQ ID NO: 1. This fragment of SEQ ID NO: 1 can be coded for example by a nucleic acid having the nucleotide sequence of SEQ ID NO: 2. It is known that the folate receptor $Fr_\alpha$ is overexpressed in some tumors, particularly in the ovary, lung and colorectal cancer. Thus, a targeting agent comprising the aforementioned fragment targets these tumors in particular, and assists the nanoparticles of the invention to locate themselves in such tumor cells.

Any expert with ordinary skills in the art can without any efforts select further scFv fragments other than the one exemplified above, having specificity for other receptors overexpressed in the same tumors mentioned above or also in others, so as to guide the localization of the present nanoparticles towards such tumors. Also these further scFv fragments may also present, preferably, as a binding portion, a histidine sequence or histidine "tag" for the complexation of $Ni^{2+}$ according to the exemplary scheme of binding of the antibody fragment to the nanoparticles described above.

The process of preparation of the nanoparticles functionalized according to the invention can therefore be defined as comprising the following steps:

a) activation of said nanoparticle with an amphiphilic polymer to form a coating having carboxylic groups exposed on the surface of the nanoparticle;

b) preparation of a derivative of said platinum-based chemotherapeutic agent with a first amino-poly(ethylene glycol) linker;

c) functionalization of the nanoparticle activated with said derivative of the chemotherapeutic agent;

d) functionalization of the nanoparticle from the step c) with a second amino-poly (ethylene glycol) linker;

e) preparation of a derivative of said antibody fragment and its binding to said second amino-poly (ethylene glycol) linker.

According to a preferred embodiment of the invention the activation of the nanoparticles in step a) of the process is carried out in the presence of an excess of the poly (ethylene glycol) polymer, equal for example to 500 monomer units of polymer per $nm^2$ of surface of the nanocubes, this being a condition that guarantees the coating of each single nanoparticle, and consequently its subsequent functionalization.

With reference to the attached FIG. 1, a preferred embodiment of the process described above is illustrated, in which the product (1) is the nanoparticle activated with the polymeric coating having carboxylic groups on the surface obtained in step a) described above, the product (2) represents the nanoparticle functionalised with a chemotherapeutic agent through a first linker obtained in step c), the product (3) represents the nanoparticle already functionalized with the chemotherapeutic agent and a second amino-poly (ethylene glycol) linker in its turn bound to the $Ni^{2+}$ complex of the nitrilotriacetic acid obtained in step d), and finally the product (4) represents the final product, the nanoparticle with the double functionalization wherein the antibody fragment is bound, through histidine tag with a quasi-covalent bond, to the $Ni^{2+}$ complex obtained in step e).

The nanoparticles with dual functionalization of the invention not only acquire the capability to carry the chemotherapeutic drug and they do it in a targeted way towards a target tissue, as mentioned above and shown by experimental data detailed in the following but, even if so functionalized, they manage to maintain the efficiency of heat mediators required for the treatment of hyperthermia despite the presence of the polymer coating and of the functionalizations.

These nanoparticles can be used in a pharmaceutical composition, also subject of the present invention, possibly in combination with other pharmaceutically acceptable active agents, excipients, carriers and/or diluents, for use in combined oncological therapies of hyperthermia and chemotherapy with platinum-based chemotherapy agents.

The present pharmaceutical compositions can be solid compositions, such as pills, tablets, capsules, and the like, or liquid compositions, for example solutions, suspensions, emulsions, and can be administered according to any appropriate route of administration, such as in particular the intratumoral route or the parenteral route, preferably intraperitoneal.

In particular, when the nanoparticles comprise antibody fragments having specificity for the folate receptor, they will be able to localize particularly on tumor cells where this receptor is overexpressed at the cell surface, as mentioned above, and preferably in ovarian tumors.

As demonstrated in the experimental part that follows, the nanoparticles of the invention are actually internalized by the cells of these tumors and, once inside the lysosomes, the decrease in pH promotes the release of the chemotherapeutic agent in the cytosol of the cell, from which it migrates in the nucleus where it damages the DNA. At the same time, the application of an external alternating magnetic field induces the heating of the nanocubes with consequent damage to the cellular structures due to heat. The two concomitant actions of heating and DNA damage by the drug induce then the cell's death.

The following experimental examples are reported for illustrative and not limitative purposes of the present invention.

Example 1—Synthesis of the Coated and Functionalized Nanoparticles of the Invention Preparation of Magnetic Cubic Nanoparticles Maghemite nanocubes ($Fe_2O_3$) with side dimensions of 14±3 nm have been synthesized according to a procedure previously described in Pablo Guardia, A. R. et al. *J. Mater. Chem. B*, 2014 2: p. 4426-4434: in a 50 mL three-necked flask 0.353 g (1 mmol) of iron (III) acetylacetonate, 0.69 g (4 mmol) of decanoic acid and 2 mL of dibenzyl ether (DBE) were dissolved in 23 mL of squalane.

After degassing for 120 minutes at 65° C. the mixture was heated to 200° C. (3° rise per minute) and maintained at this temperature for 2.5 hours. The temperature was then increased at a rate of 7° C. per minute to 310° C. or to the reflux temperature and maintained for 1 hour. After cooling to room temperature, 60 mL of acetone was added and the solution was centrifuged at 8500 rpm. The supernatant was then discarded and the black precipitate dispersed in 2-3 mL of chloroform: this washing procedure was repeated for at least two more times. Finally, the collected particles were dispersed in 15 mL of chloroform. The concentration of the final nanocubes was determined by ICP-AES analysis.

Preparation of the Polymer Coating on the Nanoparticles

The polymer coating on the individual cubic nanoparticles was obtained using a coating with an amphiphilic polymer, poly(maleic anhydride-alt-1-octadecene), as reported in Di Corato R. et al. *Journal of Materials Chemistry*, 2008 18 (17), 1991-1996. The nanocubes prepared as described above were mixed with an excess of 500 monomer units per $nm^2$ of poly(maleic anhydride-alt-1-octadecene) in $CHCl_3$. Then the solvent was removed with a rotary evaporator. Applying a vacuum that slowly decreased to 600 mbar. The entire evaporation phase has lasted 5 hours. After complete evaporation of the chloroform, borate buffer was added and the mixture was sonicated for 2 hours at 50° C. The nanocubes were concentrated using an Amicon® centrifugal filter and separated from the excess of the polymer by ultracentrifugation, using a discontinuous gradient of sucrose with the following sucrose composition in water, reported as a percentage ratio: 20%, 40% and 60%, layered from top to bottom of the tube for ultracentrifugation. After 45 minutes of centrifugation at a speed of 25,000 rpm, the nanocubes were collected in the middle fraction, while the free polymer remained in the upper layer. The recovered nanoparticles were washed several times to remove the sucrose in excess.

Characterization of the Coated Nanoparticles

Different characterizations have been performed by Dynamic Light Scattering (DLS), gel electrophoresis and Transmission Electron Microscopy (TEM).

Low-resolution TEM micrographs were obtained using a JEOL JEM-1011 microscope operating at 100 kV. The samples were prepared by drying a drop of diluted nanoparticle suspension on TEM copper grids coated with ultra-thin 400 mesh carbon. Particle size distribution was analyzed using ImageJ routine analysis software. These measurements confirmed the presence of isolated nanocubes, and the presence on them of a shell of the polymeric coating.

The hydrodynamic diameter and zeta potential of the nanoparticles was measured at 20° C. by using a Malvern Zetasizer instrument on aqueous solutions of the nanoparticles, appropriately diluted. A hydrodynamic diameter of 22 nm was thus measured, and a monomodal signal with a narrow size distribution was also observed, indicating the presence of single nanoparticles, stable in water, and the absence of aggregates.

Electrophoresis was performed on 1-2% agarose gel at a voltage of 100 V for 1 hour. The results obtained showed that the nanocubes coated with the polymer were stable and able to migrate, showing no signs of aggregation. Furthermore, due to irradiation with UV light, the presence of the fluorescent band of the polymer was not detected, a sign that the nanocube sample was free from polymer in excess.

The Specific Absorption Rate (SAR) of the coated nanoparticles was also determined by exposing their aqueous solution to an alternating magnetic field generated by a loop in a commercial device (DM100 Series, nanoScale Biomagnetics Corp.). The SAR values were measured at two different frequencies, 110 kHz and 301 kHz and at different amplitudes of the magnetic field in the range between 12 kAm−1 and 24 kAm−1, showing a linear increase proportional to the force of the applied magnetic field, such as expected for superparamagnetic nanoparticles. Their behavior in viscous media consisting of mixtures with different concentrations of water and glycerol was also determined, noting that the nanocubes maintained high SAR values regardless of the viscosity of the media used, thus showing themselves suitable for an effective treatment of hyperthermia on cells. Finally, by means of AC susceptibility measurements, the process of magnetic relaxation of the nanocubes on solutions of the nanocubes in water and in water-glycerol mixtures with different viscosities having a fixed iron concentration of 1 g/L was investigated. The data found indicated for the nanocubes a value of the anisotropy constant of 11.9 kJ/m$^3$, a value very close to that of pure magnetite, and a magnetic relaxation of the nanocubes with a Neel mechanism regardless of the viscosity of the medium in which they were dissolved.

Preparation of PEG-Oxaliplatin of Formula (I)

was treated with CuSO$_4$ (204 mg, 1.27 mmol) and sodium L-ascorbate (1.26 g, 6.37 mmol). The solution was mixed at room temperature for 15 minutes and then azido-PEG-amino-Trt (1) (207 mg, 0.25 mmol) was added in a solution of H$_2$O/MeOH (4 mL, 1:1).

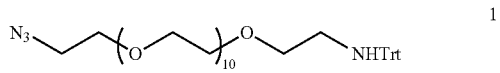

1

The mixture thus formed was mixed at room temperature for 24 hours before being treated with QuadraSil® AP resin to remove copper in excess. After 20 minutes of incubation, the resin was filtered, washed with MeOH and the solvent evaporated under reduced pressure. The resulting product was purified by flash chromatography (1-10% MeOH in CH$_2$Cl$_2$) to give 178 mg of compound 8 in the form of a light yellow oil [71%, R$_f$=0.54 (10% MeOH/CH$_2$Cl$_2$)].

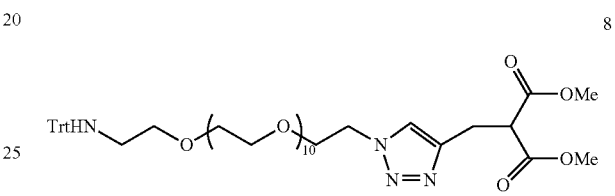

8

A solution of [Pt (Cl$_2$) (1R, 2R)-DACH)] (cis-dichloro (cyclohexane-trans-1,2-diamino) platinum (II) (34 mg, 0.09 mmol) in H$_2$O (2 mL) was treated with AgNO$_3$ (32 mg, 0.19 mmol). The mixture was protected from light, with aluminum foil, and mixed under an atmosphere of Ar at 60° C. for 20 hours. After this time, the solution was cooled to temperature environment, filtered on celite and washed with H$_2$O (3×2 mL). The solvent was concentrated under reduced pressure to about 1 mL of solution of [Pt (NO$_3$)$_2$ (NH$_2$CH$_2$CH$_2$NH$_2$)]. The compound 8 (30 mg, 0.03 mmol) was dissolved in MeOH (1 mL) and treated in an aqueous solution of NaOH (5 M, 320 μL, 0.16 mmol) After mixing at room temperature for 12 hours and after confirming the disappearance of the starting material with HPLC-MS, the solvents were concentrated under reduced pressure and the solid dried under vacuum. The resulting solid residue was treated with an aqueous solution of Pt(NO$_3$)$_2$ (NH$_2$CH$_2$CH$_2$NH$_2$)] previously prepared and the solution (I)

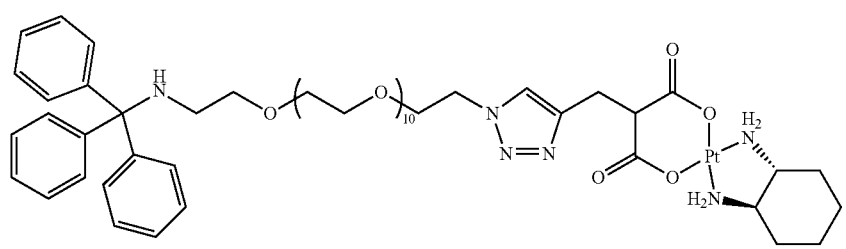

An oxaliplatin derivative with an amino-polyethylene glycol group (PEG-oxaliplatin) protected at the amino group with a triphenylmethyl group (hereinafter Trt, trityl), with a molecular weight Mn of about 1000 g/mol, having the formula (I) illustrated above.

A solution of dimethyl 2-(prop-2-in-1-yl)malonate (48 mg, 0.28 mmol) in a mixture of H$_2$O/MeOH (46 mL, 1:1)

mixed at 60° C. After 24 hours, the solution was cooled to room temperature and concentrated under reduced pressure. The resulting product was dissolved in H$_2$O and the solution cooled in an ice/water bath giving rise to a precipitate, subsequently removed by filtration and decantation. The solution was freeze-dried, yielding 35 mg of the compound of formula (I) in the form of a dark yellow solid.

Preparation of Coated Nanocubes Functionalized with PEG-Oxaliplatin

For the functionalization with the platinum-based chemotherapy drug of the nanocubes prepared as described above, the compound of formula (I) prepared as described above was used as the starting compound.

The compound of formula (I) was dissolved in methanol at a concentration of 2 mg/mL. For the deprotection from triphenylmethyl, 1 g of Amberlite IR-120 resin, previously washed several times with methanol, was added to 1 mg of compound (I) in methanol, and the mixture was subjected to vigorous stirring. After 12 hours, the so-obtained compound was filtered and analyzed by TLC to verify the deprotection. The deprotected end product was dissolved in methanol at a concentration of 1 mg/mL.

The polymer-coated cubic nanoparticles prepared as described above (0.1 µM) dissolved in 500 µL of a 1:3 mixture of borate buffer (pH=9) and water, were incubated for 10 minutes with 12.7 mM of 1-ethyl-3-(3-(dimethylaminopropyl)-carbodiimide (EDC; 127,000 molecules per nanoparticle). Then 0.05 mM of the deprotected oxaliplatin derivative as described above (Mn=1,000 g/mol; 500 molecules per nanoparticle) were added and the mixture was left to react for 4 hours. The nanocubes were washed 5 times with borate buffer using an Amicon® filter (cutoff 100,000 g/mol) until the supernatant was cleaned from the reagents in excess.

Preparation of PEG-NTA-Ni

Scheme 1

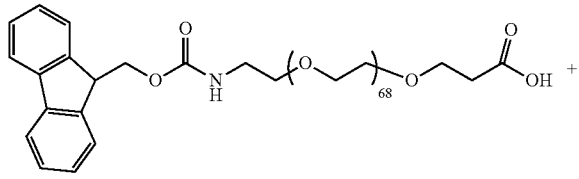

Fmoc-PEG-COOH

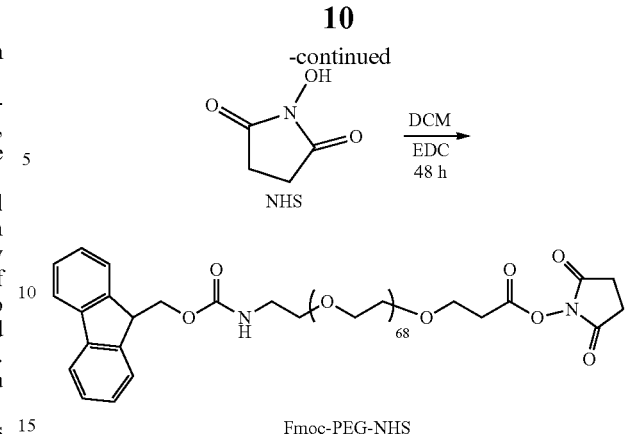

Fmoc-PEG-NHS

The derivative with amino-polyethylene glycol (PEG) of the complex with $Ni^{2+}$ of nitrilotriacetic acid (NTA) was prepared, hereinafter referred to as PEG-NTA-Ni, for a further functionalization of the nanocubes.

According to Scheme 1 above, Fmoc-PEG-COOH (Mn=3,000 g/mol) was reacted with N-hydroxysuccinimide (NHS) to activate the carboxyl group. In particular, 200 mg of PEG (0.07 mmol) were dissolved in anhydrous dichloromethane under nitrogen. Then 1-ethyl-3-(3-dimethylaminopropyl) carbodiimide (EDC) (0.35 mmol; 5 eq.) and NHS (0.35 mmol; 5 eq.) have been added and the mixture was kept under stirring in a nitrogen atmosphere for 1 hour at 6° C. Subsequently, the reaction was allowed to proceed for 48 hours at room temperature. The product was extracted with water and analyzed by $^1$H-NMR spectroscopy with a 400 MHz Bruker AV-400 spectrometer in DMSO-$d_6$ which confirmed the formation of the desired product Fmoc-PEG-NHS.

Scheme 2

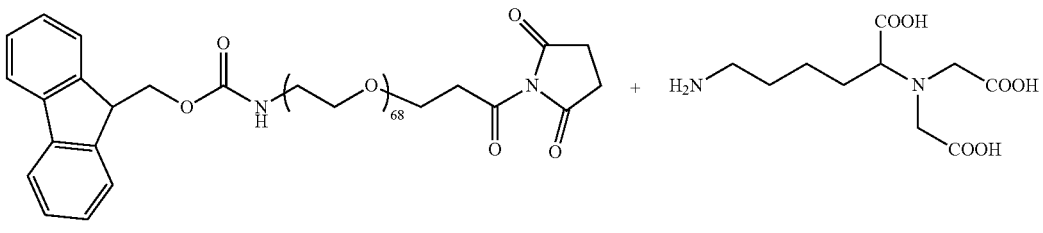

Fmoc-PEG-NHS

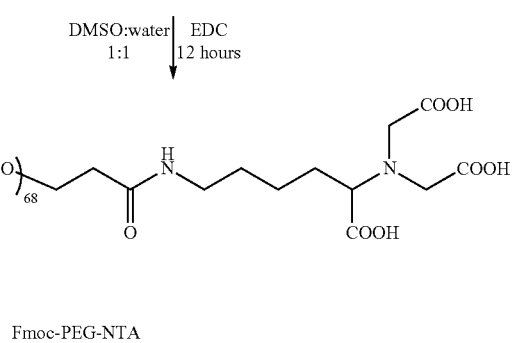

Fmoc-PEG-NTA

The Fmoc-PEG-NHS compound prepared as described above (200 mg; 0.07 mmol) was dissolved in a mixture of DMSO and water 1:1 (20 ml final volume). Na, Nα-bis (carboxymethyl)-L-lysine (0.14 mmol; 2 eq.) and EDC (1.3 mmol; 20 eq) were added and the solution was stirred for 12 hours. The product obtained was then dialyzed for 72 hours against water using an RC membrane with a cut-off of 1,000 g/mol. Using a rotary evaporator, the water was then evaporated and the derivative of the nitrilotriacetic acid with protected amino-polyethylene glycol indicated in Scheme 2 as Fmoc-PEG-NTA was obtained.

The product thus obtained was then subjected to deprotection of the amino group, then reacted with a $Ni^{2+}$ salt to obtain the desired end product PEG-NTA-Ni, as illustrated below in Scheme 3.

Fmoc-PEG-NTA was dissolved in a mixture of dichloromethane and ethanolamine 1:1 to deprotect the amino group. The mixture was stirred for 12 hours and the final $NH_2$—PEG-NTA product was purified by dialysis against water using an RC membrane with 1,000 g/mol cut-off for 72 hours.

The preparation was repeated with the same reagents and under the same conditions starting from nanocubes with the polymeric coating, without the functionalization with oxaliplatin.

Binding of the Functionalized Nanocubes to the Antibody

A 0.1 μM solution of nanocubes coated and functionalized with PEG-NTA-Ni alone or functionalized also with PEG-oxaliplatin, prepared as described above, were incubated in parallel experiments with 4 μM (50 μg) of a variable fragment to single chain of human antibody C4, (C4 scFv), having amino acid sequence SEQ ID NO: 1. Incubation was carried out in 500 μL of 0.1 M saline phosphate buffer (Phosphate Buffer Saline, PBS), pH 7.4 at 4° C. for 12 hours under light shaking. After this incubation period, the nanocubes were washed with PBS using an Amicon® filter with 100,000 g/mol cut-off until the supernatant was free from the reagent in excess.

Experiments on the Nanocubes of the Invention

Antibody-Binding Experiments Attached to the Nanocubes

Flow cytometry experiments (FACS analysis, Fluorescent Activating Cell Sorting) were conducted to demonstrate the

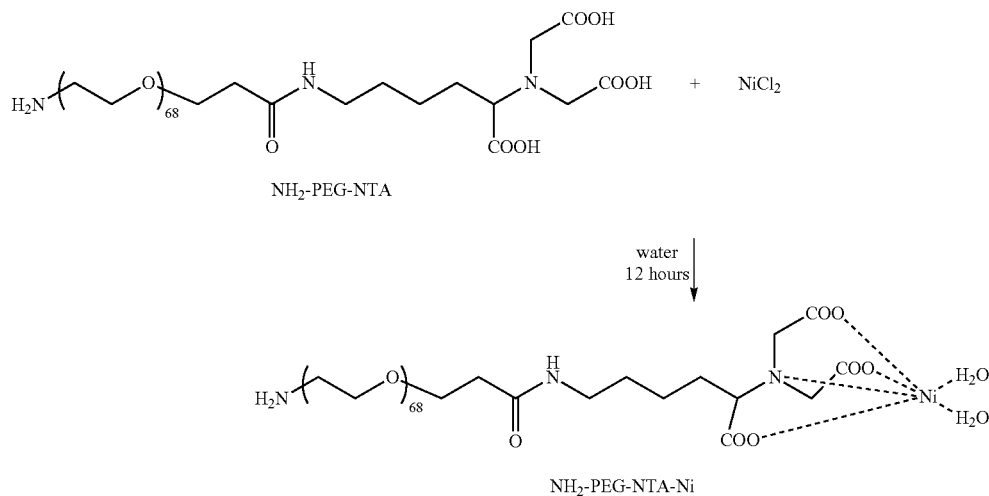

Scheme 3

$NH_2$—PEG-NTA (200 mg; 0.07 mmol) was dissolved in 20 ml of water and incubated with $NiCl_2$ (0.7 mmol; 10 eq.) for 2 hours. The product thus obtained was then dialyzed for 72 hours against water using an RC membrane with a cut-off of 1,000 g/mol. The final $NH_2$—PEG-NTA-Ni product was obtained in the form of a greenish powder after lyophilization and stored at −20° C.

Functionalization of the Nanocubes with PEG-NTA-Ni

Nanocubes functionalized with PEG-oxaliplatin prepared as described above (concentration of 0.1 μM nanocubes) were dissolved in a 1:3 mixture of borate buffer (pH=9) and water, incubated with 12.7 mM of EDC (127,000 molecules per iron molecule) for 10 minutes. Then 0.55 mM of $NH_2$—PEG-NTA-Ni prepared as described above were added (Mn=3262 g/mol) (5,500 molecules for nanoparticles) and the mixture was reacted for 4 hours. A sample functionalized with $NH_2$—PEG-carboxy was synthesized and used as a control. The nanocubes were finally washed 5 times with borate buffer using an Amicon® filter with 100,000 g/mol cut-off until the supernatant was cleaned from the reagent in excess.

specificity of the antibody bound to the nanocubes for the target and the desired cell type. Different types of cell lines have been used, which express or do not express folate receptors; in particular, four cell lines were studied: KB and IGROV-1 (cells with a high natural expression of folate receptors), A431-tFR (A431 cells transfected with a vector containing the folate receptor gene α-FR) and A431-MOCK (A431 cells transfected with an empty vector, which do not express the folate receptor). The A431-tFR and A431-MOCK cells provided by the IRCSS Foundation, National Cancer Institute, Milan, Italy, were grown in the modified Dulbecco culture medium (DMEM, Merck, Kenilworth, USA). IGROV-1 cells (ATCC, UK) were cultured in RPMI-1640 (RPMI-1640, Merck, Kenilworth, USA). The KB cells (ATCC, UK) were cultured in RPMI-1640 without folic acid (RPMI-1640 without folic acid, Merck, Kenilworth, USA). All culture media were added with 10% inactivated fetal bovine serum (FBS), 1% penicillin-streptomycin and 1% glutamine at 37° C., 95% humidity with 5% CO2. The cells were divided every 3-4 days before reaching confluence.

Figure 2:
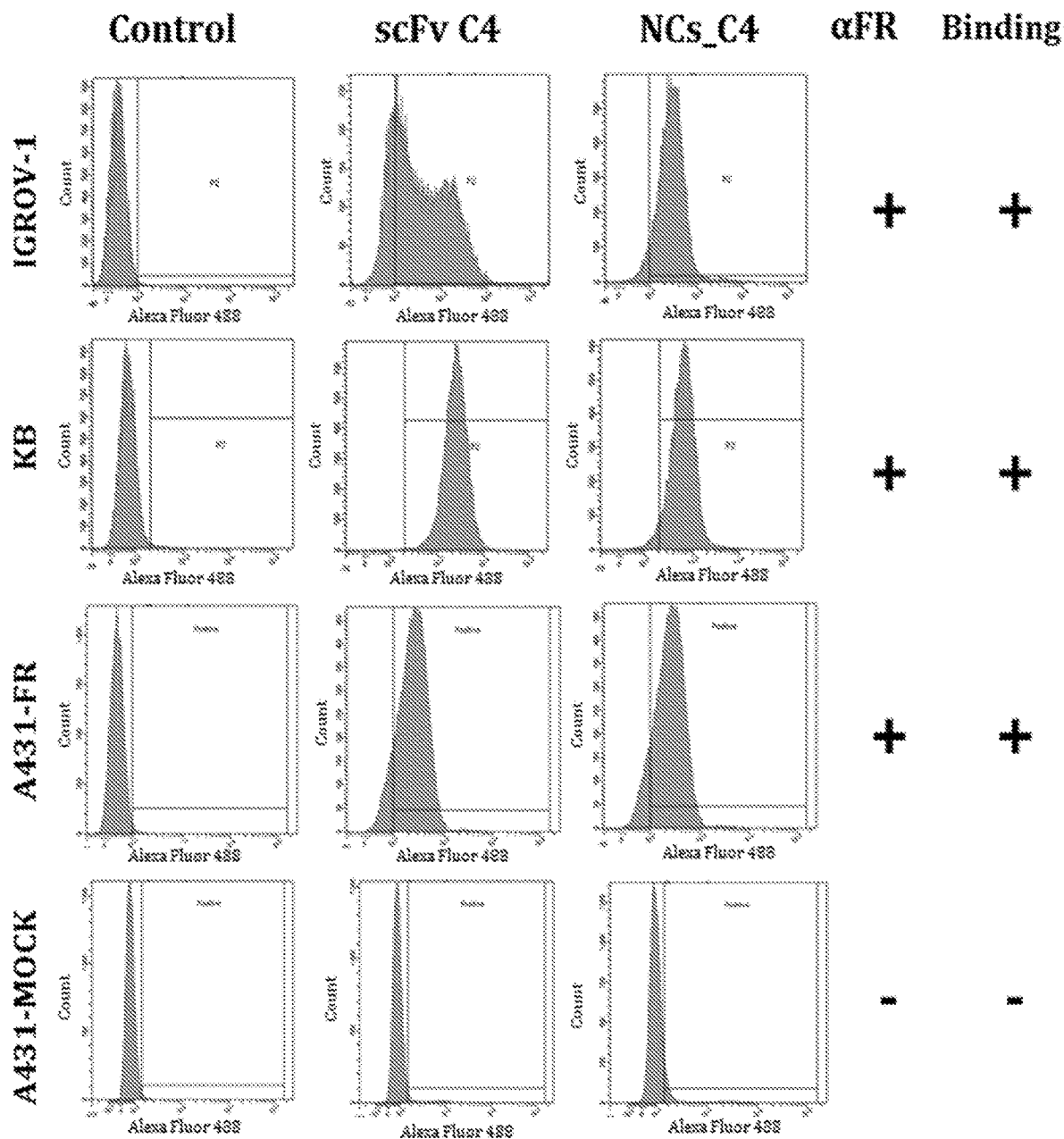
FIG. 2 consists of graphs showing the fluorescence intensity vs. the count, or number of units, of the cells in cytometric analysis experiments to verify the binding of the nanocubes of the invention to cells of several cell lines, as described in the experimental part that follows.

In these experiments, the functionalized nanocubes of the invention comprising the antibody fragment in a quantity of 0.025 mg/mL were incubated in PBS at 4° C. for 1 hour with $5\times10^5$ cells of the cell lines indicated above. As a negative control, the non-functionalised nanocubes with polymer coating were used. Then, after three washes, the cells were incubated for 1 hour at 4° C. with the primary antibody that binds to the myc sequence of the C4 antibody fragment. Following a wash in PBS a secondary antibody conjugated to the fluorescent probe Alexa-488 was added to the cells, capable of binding the Fc portion of the primary antibody. As shown in the graphs of FIG. 2, which show the intensity of fluorescence vs. cell count, nanocube binding was demonstrated for IGROV-1, KB and A431-FR cells, while no binding was found for A431-MOCK cells that did not express the folate receptor. In light of these results, it can be concluded that the cubic nanoparticles of the invention functionalized as described above specifically recognized their target, also showing that they could do it on different cell lines.

Evaluation of the Toxicity of PEG-Oxaliplatin Attached to the Nanocubes

Figure 3:
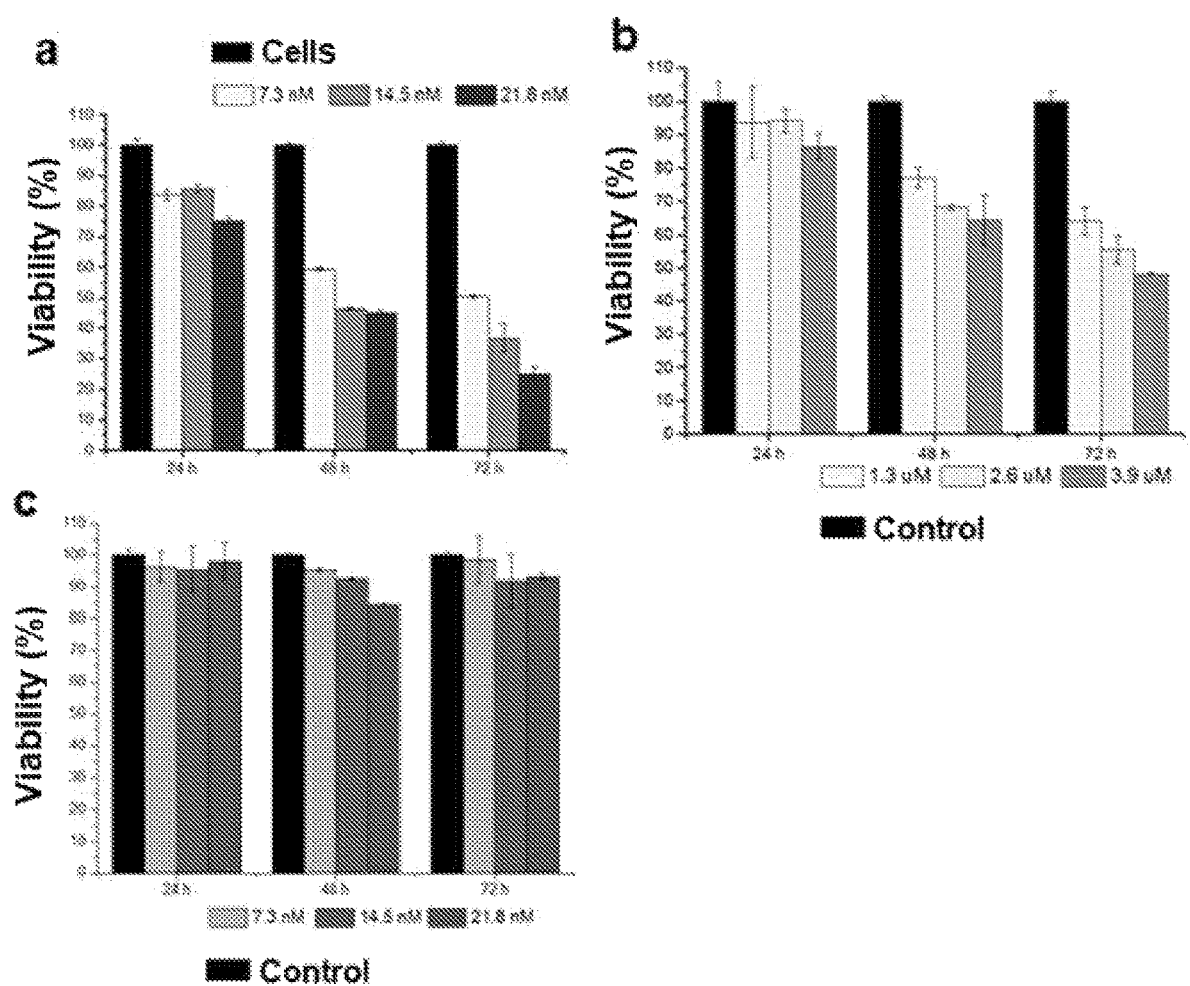
FIGS. 3a and 3b illustrate in histogram form the percentage of vitality detected with blue Presto analysis of cell samples incubated with the nanocubes of the invention for different periods of time and at different concentrations, as described later on in the experimental part.

Cytotoxicity studies have been conducted to confirm the activity of the platinum-based chemotherapeutic agent attached to the nanocubes. IGROV-1 cells were incubated with nanocubes functionalized with oxaliplatin and antibody (in FIG. 3a indicated as NCs_OHP_C4) for 24, 48 and 72 hours at Fe concentration equal to 0.05 g/L, 0.1 g/L and 0.15 g/L, corresponding to 1.3, 2.6 and 3.9 µM of oxaliplatin chemotherapeutic agent. Cell viability has been verified in an assay with Presto blue. Serious toxicity was observed after 48 hours of incubation, which increased after 72 hours of incubation (FIG. 3a). The toxicity of the chemotherapeutic agent alone was administered, administered to the cells for 24 hours, 48 hours and 72 hours at the concentration of oxaliplatin corresponding to the same quantity loaded on the nanocubes. As shown in FIG. 3b, the free drug has a moderate toxicity at the tested concentrations, lower than that found for the drug loaded on the nanocubes in the system of the present invention. Without wanting to be bound to a theory, the effect of increased toxicity of oxaliplatin when attached to nanocubes compared to when it is in free form could be explained by a greater amount of drug that the nanocubes would be able to carry within the cells, thus significantly limiting the ability of the cells to repair the damage caused by the drug. It is also important to note that in these experiments the control consisted of nanocubes with polymeric coating, functionalised with PEG-NTA-C4, but lacking oxaliplatin, prepared as described above. As can be seen in FIG. 3c the control has no toxicity on the cells, indicating the perfect biocompatibility and non-toxicity of the present drug release system, including the nickel bound to the nanocubes and the nanocubes themselves.

Figure 4A:
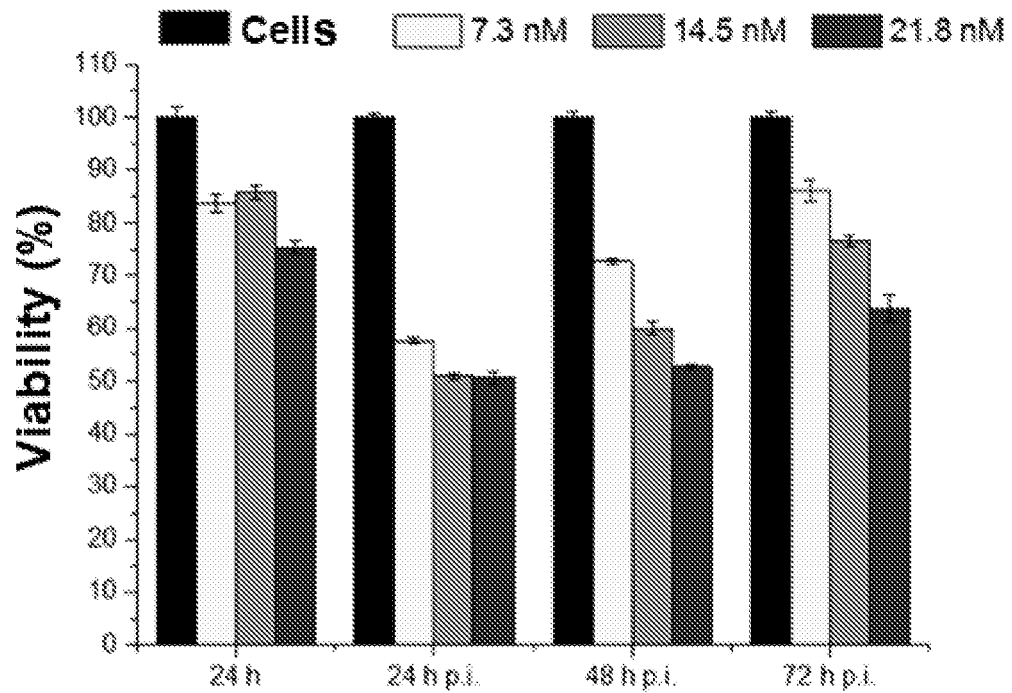
FIGS. 4a-c show, in the form of histograms, the data of cellular viability percentage detected by analysis with blue Presto for cells incubated with the nanocubes of the invention after a prolonged time of treatment, as described in the following.
Figure 4B:
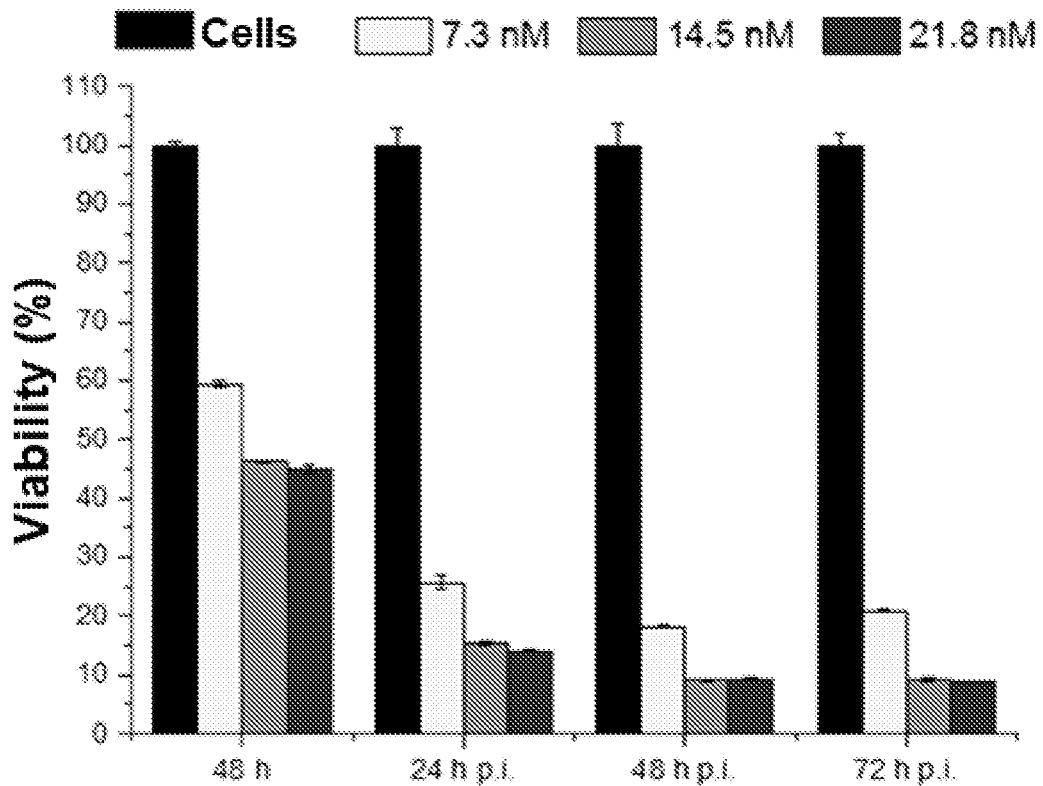
Figure 4C:
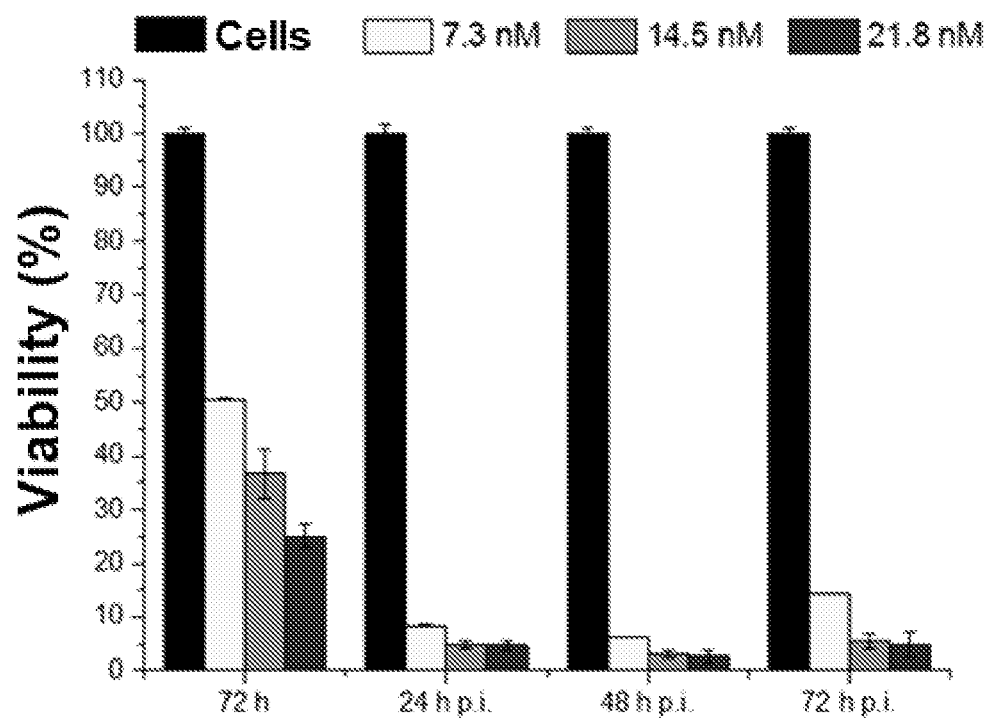

Cytotoxicity data were also collected for longer-time treatments, to verify the toxicity of oxaliplatin loaded on the nanocubes according to the invention over extended periods of time. In fact, since the action of platinum-based chemotherapy drugs involves their interleaving within the cell's DNA, the adverse effects of treatment with these drugs should be more evident at longer times after exposure to the drug. Then, after exposure of the IGROV-1 cells to the nanocubes functionalized with antibody and drug for 24, 48 and 72 hours of treatment respectively, the supernatant was removed and the cells were kept in a fresh culture medium for a further 24, 48 or 72 hours. The viability of these cells was verified by analysis with blue Presto immediately after direct exposure to the nanocubes and at 24, 48 and 72 hours after incubation. In FIG. 4a you can see how the cell viability decreases after 24 hours of treatment (post-incubation, p.i.) for the next 24 hours and then goes up again after 48 and 72 hours post-incubation. Instead, for the treatment at 48 hours the vitality decreases again for the next 72 hours, indicating that the platinum-based chemotherapy drug is still active inside the cells (FIG. 4b). In the case of treatment lasting 72 hours, toxic effects p.i. they are even more serious (FIG. 4c).

Hyperthermia Experiments in Combination with the Release of the Chemotherapeutic Agent Hyperthermia experiments were conducted on cells treated with the invention's nanocubes to monitor the efficiency of nanoparticles in killing tumor cells with heat and improving the toxicity mediated by oxaliplatin. In practice, $3\times10^6$ IGROV-1 cells were incubated with 5.5 g of Fe/L of invention nanocubes functionalized with oxaliplatin and NCs-PEG-Pt-C4 antibody fragment, and exposed to a magnetic field of 27 kA m$^{-1}$ at frequency of 182 kHz, so as not to exceed the biological limit (Hf=$5\times10^9$ A m$^{-1}$ s$^{-1}$). Two consecutive 30-minutes hyperthermia treatments were then performed, each with a maximum temperature reached in these conditions of 42° C. Also included in this study were: untreated cells, cells incubated with nanocubes functionalized only with antibody without oxaliplatin (exposed and not exposed to hyperthermia), and cells incubated with nanocubes functionalized with antibody and oxaliplatin not exposed to hyperthermia. A control experiment was also performed by incubating the cells with free oxaliplatin at the same amount of platinum loaded on the nanocubes (28 µg of platinum, corresponding to 140 µM of oxaliplatin).

Figure 5A:
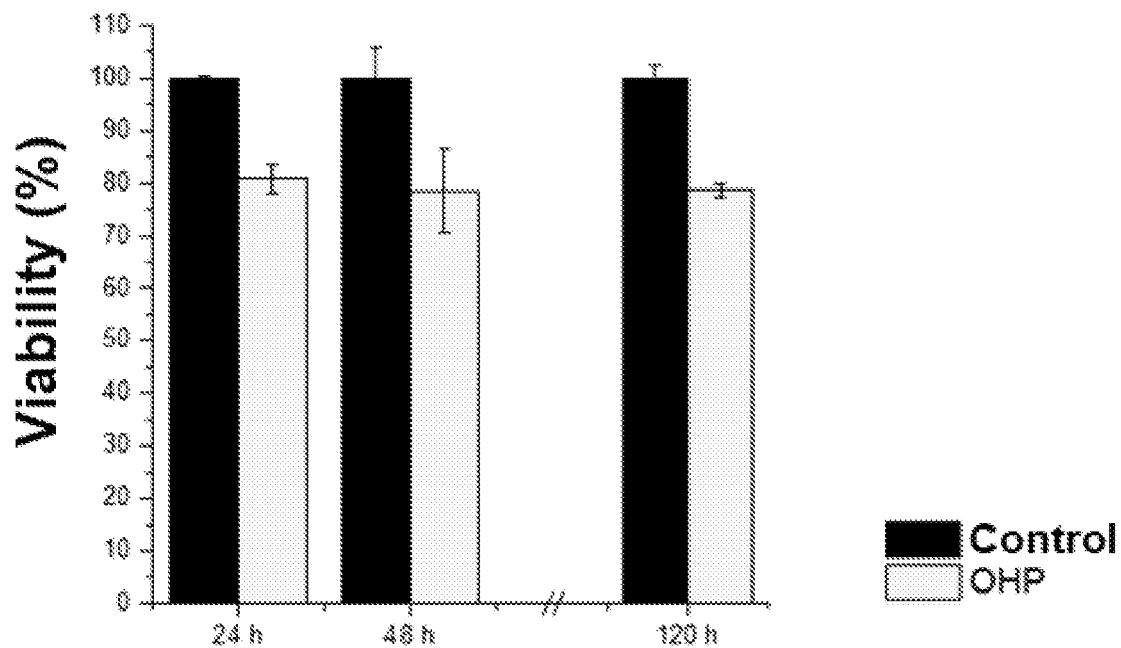
FIGS. 5a-c illustrate, again in the form of histograms, how the percentage of cell viability, detected by analysis with Presto blue of cell samples, varies when the samples are incubated with free oxaliplatin (OHP in FIG. 5a), since the samples are incubated instead with oxaliplatin loaded on nanocubes without and with hyperthermia treatment.
Figure 5B:
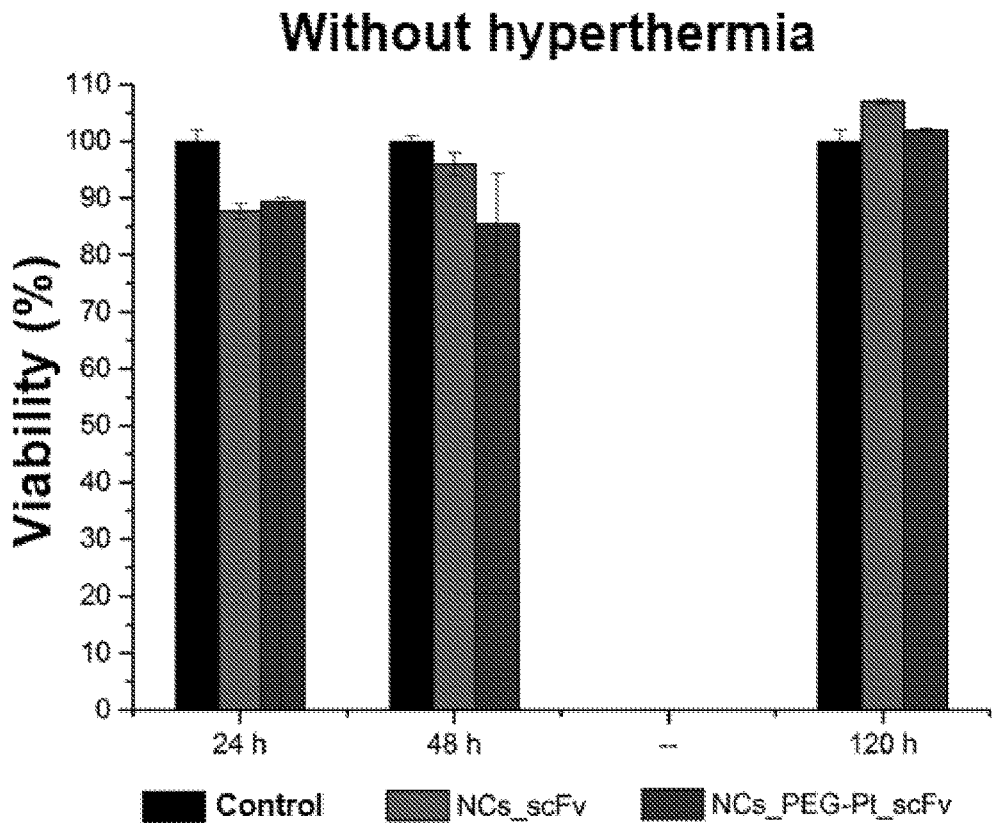
Figure 5C:
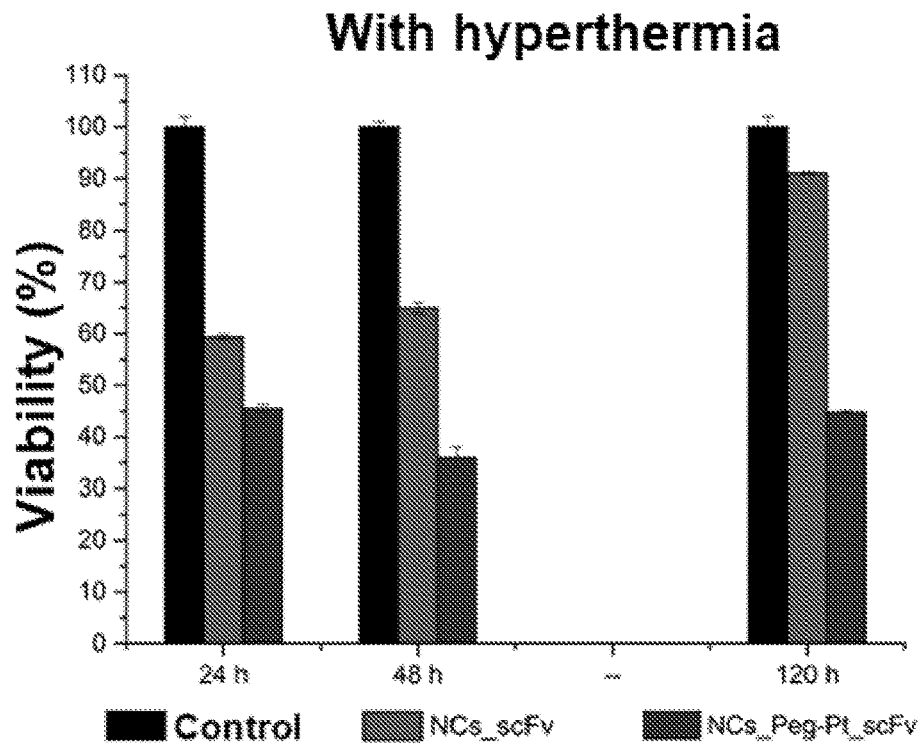

After the hyperthermal treatment, the cells were washed to remove excess nanocubes present and re-seeded in a fresh culture medium ($5\times10^4$ cells per well for each cell sample), so as to monitor their vitality at 24, 48 and 120 hours after treatment, with an assay with blue Presto. The viability of cells treated with free oxaliplatin was slightly affected by the treatment (FIG. 5a). Instead the treatment of cells with nanocubes functionalized with the antibody and with the nanocubes also functionalized with oxaliplatin in the presence of hyperthermia has significantly modified cell viability already at 24 hours (FIG. 5c in comparison with FIG. 5b). However, the vitality compared to 48 hours between the two experiments with and without hyperthermia was even more significant: while the cells treated with the nanocubes functionalized with the antibody (NCs_scFv) and exposed to hyperthermia began to show a recovery, the vitality of the exposed cells to the nanocubes also functionalised with oxaliplatin and treated with hyperthermia, they were further compromised. After 120 hours, the combined and concomitant action of hyperthermia and release of the chemotherapeutic agent made the cells unable to recover their growth (vitality of about 40% at 120 hours). This did not occur for cells treated with nanocubes lacking of the functionalization with oxaliplatin (95% viability at 120 hours).

Quantification of Intracellular Fe and Pt

Cell samples incubated with the invention's nanocubes functionalized with antibody and oxaliplatin (after hyperthermal treatment), as described above, were digested according to standard acid digestion procedure of samples for elemental analysis up to a complete digestion of the cellular components and of the iron oxide nanoparticles. The intracellular concentration of Fe and Pt was measured by atomic emission spectrometry with an inductively coupled plasma source ICP-AES. Table 1 below shows the data obtained for untreated cells, cells treated with functionalized nanocubes of the invention without hyperthermia and with hyperthermia respectively.

TABLE 1

| Sample | µmol Fe/$10^6$ cells | nmol Pt/$10^6$ cells |
|---|---|---|
| Cells | 0.00055 | * |
| Cells treated with NCs-PEG-Pt-scFv, without hyperthermia | 0.08 | 2.3 |
| Cells treated with NCs-PEG-Pt-scFv, with hyperthermia | 0.4 | 10.7 |

* data below the sensitivity threshold of the instrument.

Surprisingly, therefore, the cells treated also with hyperthermia show that they contain a quantity of the two elements about five times higher than that found in the sample not treated with hyperthermia. This is also consistent with the toxicity detected for the two samples, as described above, and indicates that hyperthermia treatment may increase the internalization of the nanocubes of the invention in the cells.

Analysis with Confocal Laser Scanning Microscope (CLSM)

Figure 6:
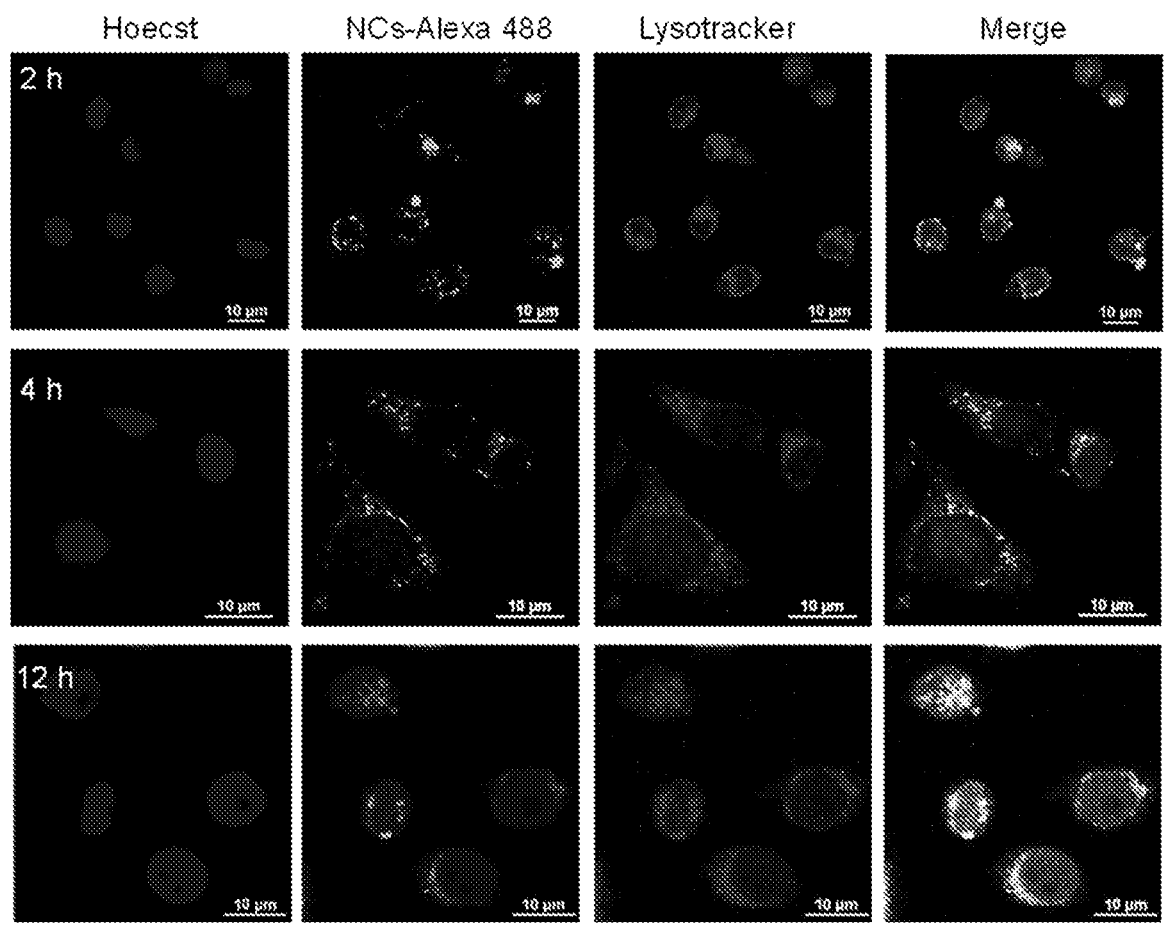
FIG. 6 shows images acquired with confocal laser scanning microscopy (CLSM) of cells incubated with the present nanocubes at different incubation times, visualized in different ways, as described below in detail.

In order to demonstrate with further data the binding of the functionalized nanocubes of the invention to the cells, images were acquired with confocal laser scanning microscopy at different times of incubation at 37° C. of IGROV-1 cells with nanocubes, after 2 hours, 4 hours and 12 hours. FIG. 6 shows the images obtained at these times with different modes of marking at different wavelengths, i.e. on a single nuclear marking channel (Hoechst, excitation wavelength of 405 nm), with nanoparticle fluorescence (fluorescent probe Alexa-488, excitation wavelength of 488 nm), lysosomes (cells labeled with Lysotracker, excitation wavelength of 570 nm), and finally fusion images of all single individual channels. From these images, it is clearly visible that after 2 hours of incubation most of the nanocubes were located at the cell membrane, while after 4 hours of incubation the progressive internalization of the nanoparticles was clearly observed in a manner dependent on the endocytosis, as indicated by the localization of the green signal of the nanoparticles and by the red signal of the Lysotracker marker). After 12 hours of incubation the complete localization of the nanocubes with lysosomes was observed, indicating a complete internalization of the nanocubes in the cells.

Study of the Mechanism of Induction of Toxicity Linked to Platinum Release

Firstly, in a test tube, the release of platinum from the citrated buffer nanocubes at different pH was verified, according to the expected acidity values for endosomes, late endosomes and lysosomes (pH=5.5, 5 and 4.5 respectively). It has thus been verified that the release of platinum is pH dependent and that the maximum amount of platinum released is obtained at the lowest pH, i.e. at pH 4.5, which corresponds to the pH of the lysosomal environment.

Furthermore, once released from the nanocubes, platinum must be incorporated into the cell nuclei and must form crosslinks with the DNA. In fact, its toxicity depends on the impossibility for cells to replicate and transcribe their genetic makeup due to the presence of platinum-DNA complexes. Thus, to evaluate the presence of cross-linking in the DNA of cells treated with nanocubes, a Comet assay was performed, whose results are illustrated in the images in FIG. 7, acquired with a confocal microscope. In this experiment, the cell samples examined of IGROV-1 cells were incubated with the nanocubes with antibody but without platinum (in FIG. 7 indicated as NCs_C4) and with the nanocubes of the invention with antibody and oxaliplatin (indicated in the figure as NCs_OHP_C4) for 24, 48 and 72 hours, so they were treated with $H_2O_2$ hydrogen peroxide. As a control, IGROV-1 cells were used, treated with the same nanocubes, with and without platinum, but without treatment with hydrogen peroxide.

Figure 7:
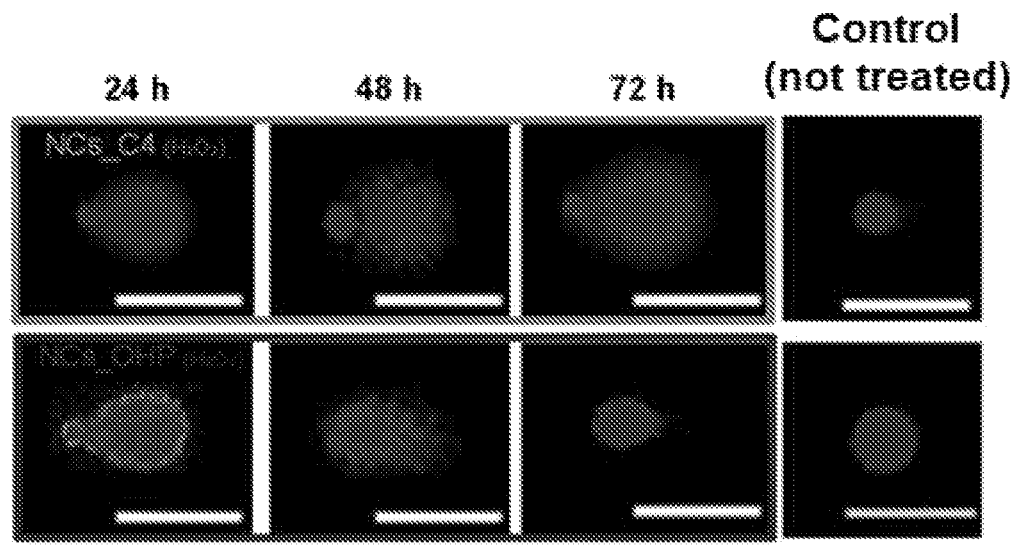
FIG. 7 shows the images acquired by confocal microscopy of cellular samples incubated at different times with the nanocubes of the invention (NCs_OHP_C4) and with the nanocubes functionalized with antibody fragment but without chemotherapeutic agent (NCs_C4) and subjected to Comet assay described in the following.

For cells incubated with nanocubes without platinum and exposed to hydrogen peroxide, DNA indicated traces of extensive damage (the comet shape of the trace is clearly visible in the images of FIG. 7, upper part, if compared to the respective control). For cells treated instead with platinum-containing nanocubes, DNA shows a progressive delay in migration reaching a maximum after 72 hours of exposure to nanoparticles, but there is no trace in the shape of a comet. Even if damaged by exposure to $H_2O_2$, the DNA is not free to migrate on the gel, indicating that the platinum attached to the nanocubes of the invention is able to form crosslinks with the cellular DNA, thus bringing its toxicity into the cell. The toxicity observed in the cells following treatment with functionalized nanocubes of the invention, we can conclude that it results from the combined effects of hyperthermia and toxicity induced by the platinum-based drug.

The present invention has been so far described with reference to a preferred embodiment. It is to be understood that there may be other embodiments which refer to the same inventive core, as defined by the scope of protection of the claims set forth in the following.

The invention claimed is:

1. A magnetic iron oxide nanoparticle having cubic shape, provided with a polymeric coating comprising carboxylic groups on its surface, said nanoparticle being further functionalized with a platinum-based chemotherapeutic agent and with a targeting agent comprising an scFv antibody fragment, wherein said chemotherapeutic agent and said targeting agent are both attached to different carboxylic groups of said polymeric coating, by means of amino-poly(ethylene glycol) linkers, said linkers being the same or different from each other, wherein and said linkers are covalently bound to said carboxylic groups of the coating.

2. The nanoparticle of claim 1, wherein said targeting agent comprises a scFv antibody fragment comprising a histidine tag, and wherein said amino-poly(ethylene glycol) linker intended for binding said targeting agent is an amino-poly(ethylene glycol) derivative of a $Ni^{2+}$ complex with nitrilotriacetic acid that binds to said targeting agent by complexation of $Ni^{2+}$ with said histidine tag.

3. The nanoparticle of claim 1, wherein said targeting agent comprises a scFv antibody fragment that specifically binds to Frα folate receptor.

4. The nanoparticle of claim 3, wherein said antibody fragment is a scFvC4 fragment having amino acid sequence SEQ ID NO: 1.

5. The nanoparticle of claim 1, wherein said platinum-based chemotherapeutic agent is an oxaliplatinum, and wherein said amino-poly(ethylene glycol) linker intended for binding said chemotherapeutic agent is bound to the oxaliplatinum molecule by a dicarboxylic group in the oxaliplatinum molecule.

6. A pharmaceutical composition comprising a plurality of nanoparticles of claim 1.

7. A method of treating tumors in a patient, comprising administering the pharmaceutical composition of claim 6 to a patient in need thereof.

8. The method of claim 7, wherein the pharmaceutical composition is administered as part of a combination therapy of hyperthermia and chemotherapy.

9. The method of claim 7, wherein said tumour is a tumour selected from among ovarian tumour, colorectal tumour and lung tumour.

10. A process for the preparation of the nanoparticle of claim 1, comprising:
   a) activating said nanoparticle with an amphiphilic polymer to form a coating having carboxylic groups exposed on the nanoparticle's surface;
   b) preparing a platinum-based chemotherapeutic agent derivative with a first amino-poly(ethylene glycol) linker;
   c) functionalizing the nanoparticle following activation with said chemotherapeutic agent derivative;
   d) functionalizing the nanoparticle coming from step c) with a second amino-poly(ethylene glycol) linker; and
   e) preparing a derivative of said antibody fragment and binding thereof to said second amino-poly(ethylene glycol) linker.

\* \* \* \* \*